(12) United States Patent
Vahala

(10) Patent No.: US 10,459,043 B2
(45) Date of Patent: Oct. 29, 2019

(54) REAL TIME CONTROL OF HIGH INTENSITY FOCUSED ULTRASOUND USING MAGNETIC RESONANCE IMAGING

(75) Inventor: Erkki Tapani Vahala, Hyvinkaa (FI)

(73) Assignee: Profound Medical Inc., Mississauga, ON (CA)

( * ) Notice: Subject to any disclaimer, the term of this patent is extended or adjusted under 35 U.S.C. 154(b) by 824 days.

(21) Appl. No.: 14/239,268

(22) PCT Filed: Aug. 27, 2012

(86) PCT No.: PCT/IB2012/054376
§ 371 (c)(1),
(2), (4) Date: Feb. 18, 2014

(87) PCT Pub. No.: WO2013/030746
PCT Pub. Date: Mar. 7, 2013

(65) Prior Publication Data
US 2014/0194728 A1    Jul. 10, 2014

Related U.S. Application Data

(60) Provisional application No. 61/528,906, filed on Aug. 30, 2011.

(51) Int. Cl.
*G01R 33/28* (2006.01)
*A61N 7/02* (2006.01)
(Continued)

(52) U.S. Cl.
CPC .......... *G01R 33/285* (2013.01); *A61B 5/055* (2013.01); *A61B 5/4836* (2013.01); *A61B 8/485* (2013.01);
(Continued)

(58) Field of Classification Search
CPC ... A61B 17/320068; A61B 5/00; A61B 8/485; A61B 5/055–0555; A61B 2090/374; G01R 33/20–586
See application file for complete search history.

(56) References Cited

U.S. PATENT DOCUMENTS 5,938,600 A    8/1999  Van Vaals et al.
6,044,290 A    3/2000  Vigen et al.
(Continued)

FOREIGN PATENT DOCUMENTS

EP    2489407 A1    8/2012
JP    2004358264 A    12/2004
(Continued)

OTHER PUBLICATIONS

Stafford et al. "Fast magnetic resonance thermal imaging using dynamic updating of spiral interleaves." Proc. of 22nd Annual EMBS Intl Conf, Chicago IL, Jul. 23-28, 2000. pp. 47-50. (Year: 2000).*

(Continued)

*Primary Examiner* — Angela M Hoffa
(74) *Attorney, Agent, or Firm* — Intrinsic Law Corp.

(57) ABSTRACT

A medical apparatus (300, 400, 500) comprises a high intensity focused ultrasound system (322) configured for sonicating a target volume (340) of a subject (318). The medical apparatus further comprises a magnetic resonance imaging system (302) for acquiring magnetic resonance data (356, 358, 360, 368, 374) from an imaging zone (308). The treatment volume is within the imaging zone. The medical apparatus further comprises a memory (352) containing machine executable, a control module (382, 402) for controlling the sonication of the target volume using the magnetic resonance data as a control parameter, and a processor (346). Execution of the instructions causes the processor to repeatedly acquire (102, 202) magnetic resonance data in (Continued)

real time using the magnetic resonance imaging system and control (104, 206) sonication of the target volume by the high intensity focused ultrasound system in real time using the sonication control module and the magnetic resonance data.

16 Claims, 5 Drawing Sheets

(51) Int. Cl.
*A61B 5/055* (2006.01)
*A61B 5/00* (2006.01)
*A61B 8/08* (2006.01)
*A61B 17/32* (2006.01)
*G01R 33/48* (2006.01)
*A61B 8/00* (2006.01)
*A61B 90/00* (2016.01)

(52) U.S. Cl.
CPC ........ *A61B 17/320016* (2013.01); *A61N 7/02* (2013.01); *G01R 33/4814* (2013.01); *G01R 33/4818* (2013.01); *A61B 8/565* (2013.01); *A61B 2017/320069* (2017.08); *A61B 2090/374* (2016.02)

(56) References Cited

U.S. PATENT DOCUMENTS

| | | | |
|---|---|---|---|
| 6,374,132 B1 | 4/2002 | Acker et al. | |
| 6,377,045 B1* | 4/2002 | Van Den Brink | G01R 33/4822 324/307 |
| 6,618,620 B1 | 9/2003 | Freundlich et al. | |
| 7,363,071 B2 | 4/2008 | Damasco et al. | |
| 7,840,045 B2 | 11/2010 | Guo et al. | |
| 8,653,817 B2* | 2/2014 | Busse | G01R 33/56308 324/307 |
| 8,998,889 B2* | 4/2015 | Mahon | A61N 7/02 606/27 |
| 9,205,282 B2* | 12/2015 | Mahon | A61N 7/02 |
| 9,360,544 B2* | 6/2016 | Huang | G01R 33/4804 |
| 9,971,003 B2* | 5/2018 | Kohler | A61B 5/055 |
| 9,993,196 B2* | 6/2018 | Vahala | G01R 33/4808 |
| 2004/0039280 A1* | 2/2004 | Wu | G01R 33/4804 600/412 |
| 2007/0239062 A1 | 10/2007 | Chopra et al. | |
| 2008/0033420 A1* | 2/2008 | Nields | A61B 18/18 606/27 |
| 2008/0107234 A1* | 5/2008 | Amitani | G01T 1/2018 378/98.5 |
| 2008/0242972 A1* | 10/2008 | Jung | G01R 33/5611 600/410 |
| 2008/0275331 A1* | 11/2008 | Tseng | G01R 33/4804 600/411 |
| 2008/0292167 A1* | 11/2008 | Todd | G01R 33/4804 382/131 |
| 2010/0231217 A1 | 9/2010 | Gross et al. | |
| 2010/0280356 A1 | 11/2010 | Kohler et al. | |
| 2011/0006768 A1* | 1/2011 | Ying | G01R 33/5611 324/309 |
| 2011/0137147 A1 | 6/2011 | Skliar et al. | |
| 2011/0208055 A1* | 8/2011 | Dalal | G06F 19/3481 600/439 |
| 2013/0099786 A1* | 4/2013 | Huang | G01R 33/246 324/309 |
| 2015/0126799 A1* | 5/2015 | Vahala | A61N 5/1049 600/1 |
| 2015/0190659 A1* | 7/2015 | Kohler | A61N 7/02 600/411 |
| 2016/0082288 A1* | 3/2016 | Vahala | A61N 5/1075 600/411 |

FOREIGN PATENT DOCUMENTS

| | | |
|---|---|---|
| JP | 2010069006 A | 4/2010 |
| WO | 2010122449 A1 | 10/2010 |
| WO | 2011017168 A2 | 2/2011 |

OTHER PUBLICATIONS

Kohler et al, "Volumetric HIFU Ablation Under 3D Guidance of Rapid MRI Thermometry", Medical Physics, vol. 36, No. 8, Jul. 1, 2009, p. 3521-3535.

Quesson et al, "A Method for MRI Guidance of Intercostal High Intensity Focused Ultrasound Ablation in the Liver", Medical Physics, vol. 37, No. 6, May 13, 2010,, p. 2533-2540.

Rares et al, "Local Hyperthermia With MR-Guided Focused Ultrasound: Spiral Trajectory of the Focal Point Optimized for Temperature Uniformity in the Target Region", Journal of Magnetic Resonance Imaging, vol. 12, No. 4, Jan. 1, 2000, p. 571-583.

Baudouin et al, "Real-Time Adaptive Method for Treatment of Mobile Organs by MRI-Controlled High-Intensity Focused Ultrasound", Magnetic Resonance in Medicine, vol. 57, Feb. 1, 2007, p. 319-330.

\* cited by examiner

REAL TIME CONTROL OF HIGH INTENSITY FOCUSED ULTRASOUND USING MAGNETIC RESONANCE IMAGING

CROSS-REFERENCE TO PRIOR APPLICATIONS

This application is the U.S. National Phase application under 35 U.S.C. § 371 of International Application No. PCT/IB2012/054376, filed on Aug. 27, 2012 which claims the benefit of U.S. Provisional Patent Application No. 61/528,906 filed on Aug. 30, 2011. These applications are hereby incorporated by reference herein.

TECHNICAL FIELD

The invention relates to high intensity focused ultrasound, in particular the invention relates to magnetic resonance image guided high intensity focused ultrasound.

BACKGROUND OF THE INVENTION

In recent years, magnetic resonance thermometry has been coupled with various means of heating or cooling tissue for therapy. Measuring the effect of the tissue heating or cooling allows the guiding of the therapy and also the ability to assess the effect of a therapeutic treatment on a subject.

In high-intensity focused ultrasound (HIFU) therapy, reliable real-time temperature monitoring using, e.g., Magnetic Resonance Imaging (MRI) is necessary to ensure a sufficient thermal necrosis to the target while avoiding excessive heating and damage of surrounding healthy tissues. To achieve sufficient temporal and spatial resolution, fast imaging is required preferably with a high spatial resolution while maintaining a sufficient SNR for reconstruction of reliable temperature measurements.

SUMMARY OF THE INVENTION

The invention provides for a medical apparatus, a method of operating a medical apparatus, and a computer program product in the independent claims. Embodiments are given in the dependent claims.

Presently, the state of the art in feedback calculations for the control of high intensity focused ultrasound is based on the incoming images from diagnostic scanners, such as the phase images from Magnetic Resonance (MR) scanners. Customized real-time reconstruction hardware and software has been used in Magnetic Resonance Imaging (MRI) bolus tracking and in experimental fast reconstruction methods, but no attempts have been made to create sustainable, non-diagnostic feedback loops entirely in the real-time domain.

Diagnostic image calculations are typically lengthy operations and much effort is spent to produce visually meaningful image data, at the expense of reconstruction time and complexity. Embodiments of the invention may overcome this and other problems by separating the diagnostic viewing from the real-time feedback loop, where the reconstruction can be optimized for feedback performance.

Diagnostic image calculations are typically carried out in a non-real-time environment due to the complexity and easy expandability. The non-real-time operating systems cause large jitter and performance variability in image throughput. As a result, the feedback loop optimization remains conservative due to too many unknown variables in the loop path. This invention overcomes the problem by using a soft or hard real-time operating system: tailored feedback algorithms do not have similar needs for expandability as do the constantly evolving diagnostic image reconstruction algorithms. The algorithm time-characteristics can be measured and their memory behavior optimized for minimal jitter and maximal repeatability, which helps in the design of the feedback loop parameters.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

'Computer memory' or 'memory' is an example of a computer-readable storage medium. Computer memory is any memory which is directly accessible to a processor. Examples of computer memory include, but are not limited to: RAM memory, registers, and register files. References to 'computer memory' or 'memory' should be interpreted as possibly being multiple memories. The memory may for instance be multiple memories within the same computer system. the memory may also be multiple memories distributed amongst multiple computer systems or computing devices.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to 'computer storage' or 'storage' should be interpreted as possibly being multiple storage devices. The storage may for instance be multiple storage devices within the same computer system or computing device. The storage may also be multiple storages distributed amongst multiple computer systems or computing devices.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface, which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

The Field Of View (FOV) is defined herein as meaning the volume for which an MRI image is constructed. The MRI data used to construct an MRI image is radio signals that are collected in the frequency domain. It is therefore important to note that the MRI data is converted into an image using a Fourier integral, and as a result tissues outside of the FOV contribute to the image.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

Magnetic Resonance thermometry data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonant frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical apparatus comprising a high-intensity focused ultrasound system configured for generating focused ultrasonic energy for sonicating a target volume of a subject. The medical apparatus further comprises a magnetic resonance imaging system for acquiring magnetic resonance data from an imaging zone. The treatment volume is within the imaging zone. The medical apparatus further comprises a memory containing machine executable instructions for controlling the medical apparatus. The medical apparatus further comprises a control module for controlling the sonication of the target volume using the magnetic resonance data as a control parameter. The sonication control module may be implemented in software, hardware, or as a combination of hardware and software components.

The sonication control module is adapted for using the raw magnetic resonance data for controlling the high-intensity focused ultrasound system. The medical apparatus further comprises a processor for controlling the medical apparatus. Execution of the machine executable instructions causes the processor to repeatedly acquire magnetic resonance data in real time using the magnetic resonance imaging system. By acquiring the magnetic resonance data in real time it is meant that the magnetic resonance data is acquired with a guarantee in how often the magnetic resonance data is acquired. For instance the magnetic resonance data may be provided at intervals of several tens or hundreds of milliseconds. Execution of the instructions further causes the processor to repeatedly control sonication of the target volume by the high-intensity focused ultrasound system in real time using the sonication control module and the magnetic resonance data. This embodiment may be beneficial because the control of the high-intensity focused ultrasound system by the sonication control module using the real time magnetic resonance data forms a closed feedback control loop.

In another embodiment the magnetic resonance data comprises magnetic resonance thermometry data. This embodiment may be beneficial because the sonication control module can control the high-intensity focused ultrasound system on the basis of the change in temperature of the target volume. This may be extremely desirable for a treatment where a target volume is held above or between particular temperatures for a specified period of time.

In another embodiment the magnetic resonance data comprises subsampled magnetic resonance data and image magnetic resonance data. One interpretation of 'sub-sampling' as used herein encompasses ignoring or removing the high-frequency component of k-space. For example, for a target k-space sampling matrix of dimension N (N refers here to a "high-resolution" sampling strategy, as opposed to prior art), fewer than N k-space samples are acquired, for the body coil and/or for the coil array data. In this interpretation of sub-sampling, the high frequency components are missing Another interpretation of 'sub-sampling' as used herein encompasses undersampling. In undersampling selected frequency components are not sampled. The components which are not sampled may be based on uniform or non-uniform under-sampling patterns or distributions.

The apparatus further comprises an image reconstruction module for reconstructing the image magnetic resonance data into a magnetic resonance image. The sonication control module is configured for using at least the subsampled magnetic resonance data as the control parameter. Execution of the instructions further causes the processor to repeatedly reconstruct an image using the image reconstruction module and the image magnetic resonance data. This embodiment may be particularly beneficial because it may require more time to acquire the image magnetic resonance data than the subsampled magnetic resonance data. Using the subsampled magnetic resonance data enables faster acquisition and processing of the magnetic resonance data than if image magnetic resonance data is used for controlling the sonication.

In another embodiment the magnetic resonance imaging system acquires the subsampled magnetic resonance data and image magnetic resonance data in an interleaved fashion. This may be beneficial because the subsampled magnetic resonance data can be acquired more often or more frequently than the image magnetic resonance data. Also for control of the sonication the amount of data necessary to construct an image may not be necessary. In one possible implementation of this embodiment the subsampled magnetic resonance data is acquired with a particular periodicity. The image magnetic resonance data may then be acquired less frequently. The subsampled magnetic resonance data may be used for controlling the sonication and the image magnetic resonance data may be displayed on a display for the benefit of an operator or a physician.

In another embodiment the subsampled magnetic resonance data is subsampled in comparison to the image magnetic resonance data. This may be beneficial because the subsampled magnetic resonance data may be acquired more rapidly than the image magnetic resonance data. The conversation of the image magnetic resonance data into an image may also consume time.

In another embodiment the subsampled magnetic resonance data is subsampled by undersampling in k-space. In the acquisition of magnetic resonance data measurements are typically made in k-space. Depending upon the sampling scheme an image can be acquired which contains particular data of interest. For instance if it is determined that a particular portion of k-space is relevant to a control algorithm then just this portion of k-space can be acquired. This has the benefit of accelerating the time necessary to acquire the subsampled magnetic resonance data.

In another embodiment undersampling of the k-space is performed using a predetermined sampling pattern.

In another embodiment undersampling of the k-space is performed using a random sampling pattern.

In another embodiment the undersampling of the k-space is performed by sampling k-space elements determined by a Poisson-Disk distribution.

In another embodiment the undersampling of the k-space is performed by sampling k-space within a predetermined region of k-space. For instance a keyhole type volume of k-space may be sampled.

In another embodiment the undersampling of the k-space is performed by sampling fully a kernel of k-space below a predetermined value of k and sparsely sampling above the predetermined value of k.

In another embodiment the subsampled magnetic resonance data comprises magnetic resonance navigator data. A magnetic resonance navigator data as used herein encompasses magnetic resonance data which is acquired from a limited region of interest. Typically magnetic resonance navigator data is used to monitor the internal motions of a subject by examining the motion of a portion of the subject. For instance placing a magnetic resonance navigator on the diaphragm may be used in conjunction with a model of the subject to predict the location of other organs or internal structures within a subject. An advantage of acquiring magnetic resonance navigator data is that the data may be acquired extremely rapidly.

In another embodiment the medical imaging system further comprises an elastographic ultrasound system. In the elastographic ultrasound system as used herein it encompasses an ultrasound system which causes vibrations within the subject.

An electrographic ultrasound system as used herein comprises an ultrasonic transducer and power supply which are used to produce vibrations in a vibration region of the subject. The electrographic ultrasound system may for example, but is not limited to, be used for performing ultrasound elastography or magnetic resonance imaging elastography. The target volume may be identical with the vibration region or it may be a subset of a vibration region. The electrographic ultrasound system is used to produce vibrations in the subject which may be used to identify changes in the elastic properties of tissue within the subject.

For instance tissues which are less elastic will move less and/or cause less blurring in medical images. The instructions further cause the processor to activate the electrographic ultrasound system when acquiring at least a portion of the magnetic resonance data.

The sonication control module is configured to use at least the portion of the magnetic resonance data acquired when the elastographic ultrasound system was active for controlling the sonication. For instance when the system is acquiring the magnetic resonance data when the elastographic ultrasound system is activated a pulse sequence may be use which encodes the location of spins.

The elastographic ultrasound system may cause the tissue to vibrate. If for instance the tissue is sonicated or has been heat treated the elastic properties of the tissue may change. This may then be detected by making an elastographic magnetic resonance image. This for instance may be useful in determining which portions of a subject have been successfully treated. This would have the benefit because once the elastic properties of the tissue have changed it may not be necessary to continue therapy or treatment, a different region or volume may be treated instead. This may lead to more rapid treatment of the subject.

In another embodiment execution of the instructions further cause the controller to repeatedly calculate an energy deposition map using the magnetic resonance data. The sonication control module is configured to determine sonication trajectories and timing values in accordance with the energy deposition map. This embodiment may be particularly beneficial because such an energy deposition map may be used by the sonication control module to control the sonication. For instance it may be used in a so called proportional, integral and derivative (PID) automatic temperature control algorithm. Such control algorithms are known. For example such an algorithm is disclosed in Mougenot et al., Magnetic Resonance in Medicine, pages 603-614, volume 61 (2009).

In another embodiment execution of the instructions causes the processor to broadcast the magnetic resonance data to the sonication control module. This embodiment may be particularly advantageous because the sonication control module is using the broadcast or raw magnetic resonance data. This may bypass the imaging function of the magnetic resonance imaging system completely. In some embodiments the sonication control module may strip away useless data which may accelerate the processing.

In another embodiment the sonication control module is configured to control the high-intensity focused ultrasound system without generating images from the magnetic resonance data. This may have the benefit because it may increase the rate at which the sonication control module functions.

In another aspect the invention provides for a method of operating a medical apparatus. The medical apparatus comprises a high-intensity focused ultrasound system configured for generating focused ultrasonic energy for sonicating a target volume of a subject. The medical apparatus further comprises a magnetic resonance imaging system for acquiring magnetic resonance data from an imaging zone. The treatment volume is within the imaging zone. The medical apparatus further comprises a control module for controlling the sonication of the target volume using the magnetic resonance data as a control parameter. The method comprises the step of repeatedly acquiring magnetic resonance data in real time using the magnetic resonance imaging system. The method further comprises the step of repeatedly controlling sonication of the target volume by the high-intensity focused ultrasound system in real time using the sonication control module and the magnetic resonance data. Advantages of this method have been previously discussed.

In another aspect the invention provides for a computer program product comprising machine executable instructions for execution by a processor controlling a medical apparatus. The medical apparatus comprises a high-intensity focused ultrasound system configured for generating focused ultrasonic energy for sonicating a target volume of a subject. The medical apparatus further comprises a magnetic resonance imaging system for acquiring magnetic resonance data from an imaging zone. The medical apparatus further comprises a control module for controlling the sonication of the target volume using the magnetic resonance data as a control parameter. Execution of the instructions causes the processor to repeatedly acquire magnetic resonance data in real time using the magnetic resonance imaging system. Execution of the instructions further causes the processor to repeatedly control sonication of the target volume by the high-intensity focused ultrasound system in real time using the sonication control module and the magnetic resonance data. Advantages of this computer program product have been previously discussed.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
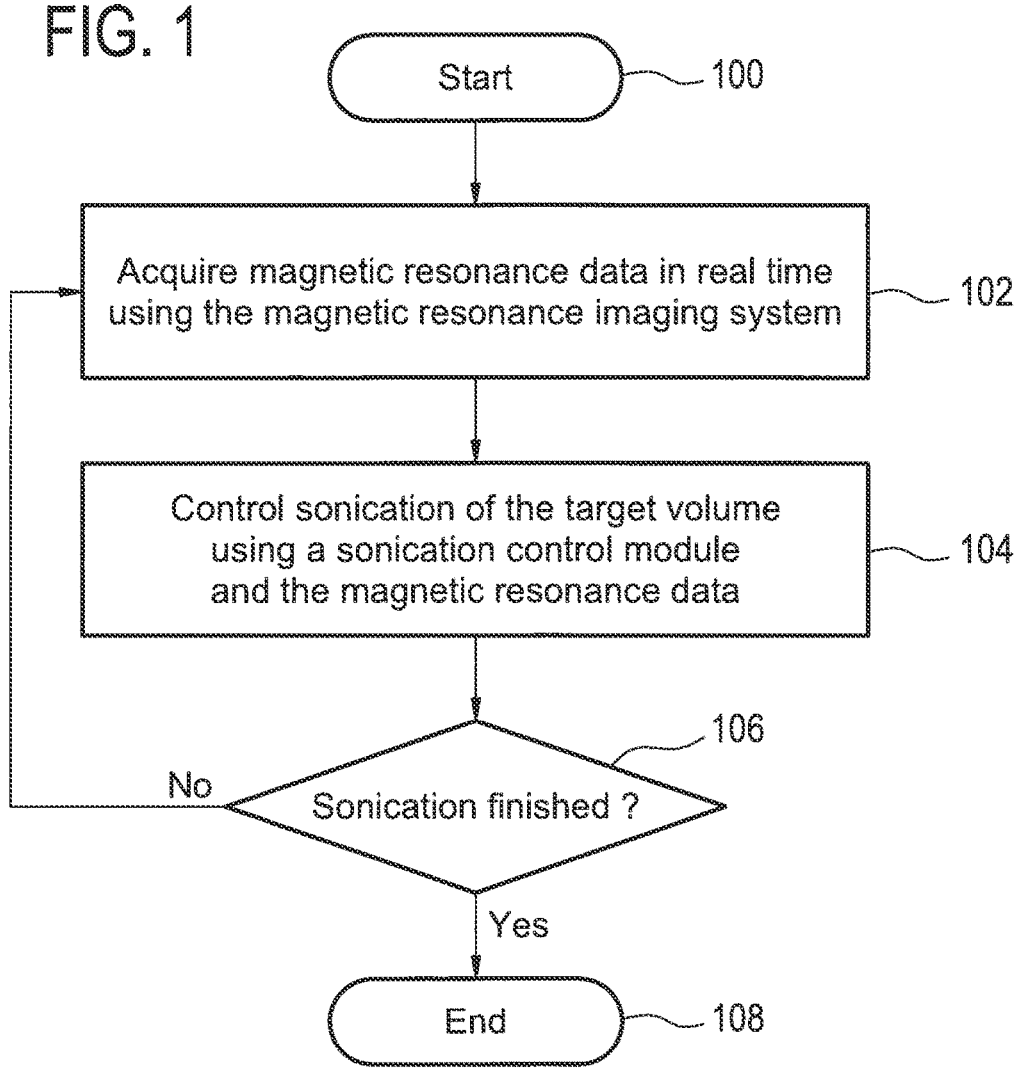
FIG. 1 shows a flow diagram which illustrates a method according to an embodiment of the invention.

FIG. 1 shows a flow diagram which illustrates a method according to an embodiment of the invention. The method starts in step 100. Next in step 102 magnetic resonance data is acquired in real time using the magnetic resonance imaging system. Next in step 104 the sonication of the target volume is controlled using a sonication control module which uses the magnetic resonance data that was acquired in real time as input. Box 106 is a decision box. If the sonication is not finished then the method returns back to step 102. Then steps 102 and 104 are repeated until the sonication is finished. After the sonication is finished the method ends in step 108.

Figure 2:
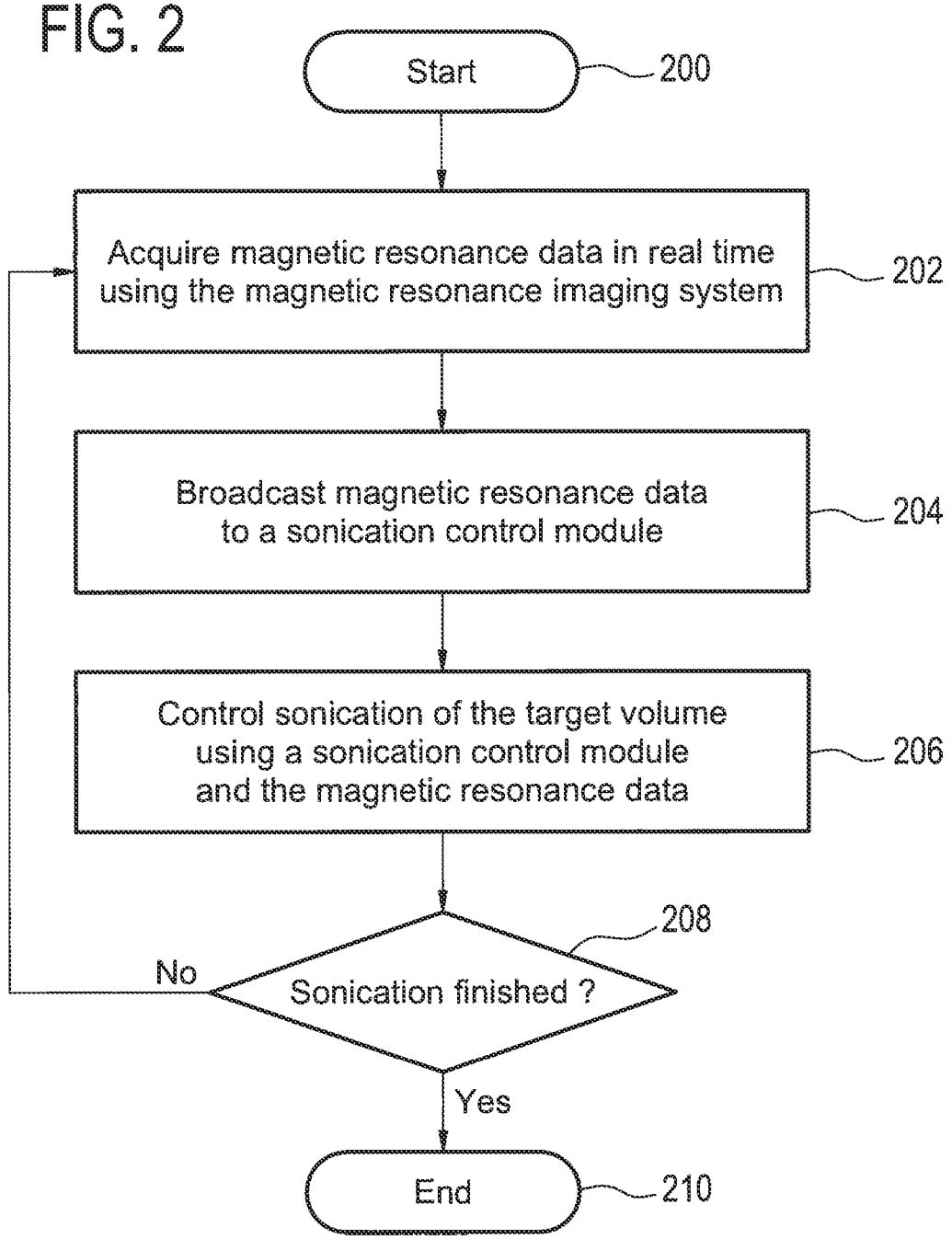
FIG. 2 shows a flow diagram which illustrates a further method according to an embodiment of the invention.

FIG. 2 shows a flow diagram which illustrates a further method according to an embodiment of the invention. The method starts in step 200. Next in step 202 magnetic resonance data is acquired in real time using a magnetic resonance imaging system. Next in step 204 the magnetic resonance data is broadcast to a sonication control module. In step 206 the sonication of the target volume is controlled using a sonication control module with the magnetic resonance data as input. Step 208 is a decision box. If the sonication is not finished then steps 202, 204, and 206 are repeated n a loop until the sonication is finished. When the sonication is finished, the method ends in step 210.

Figure 3:
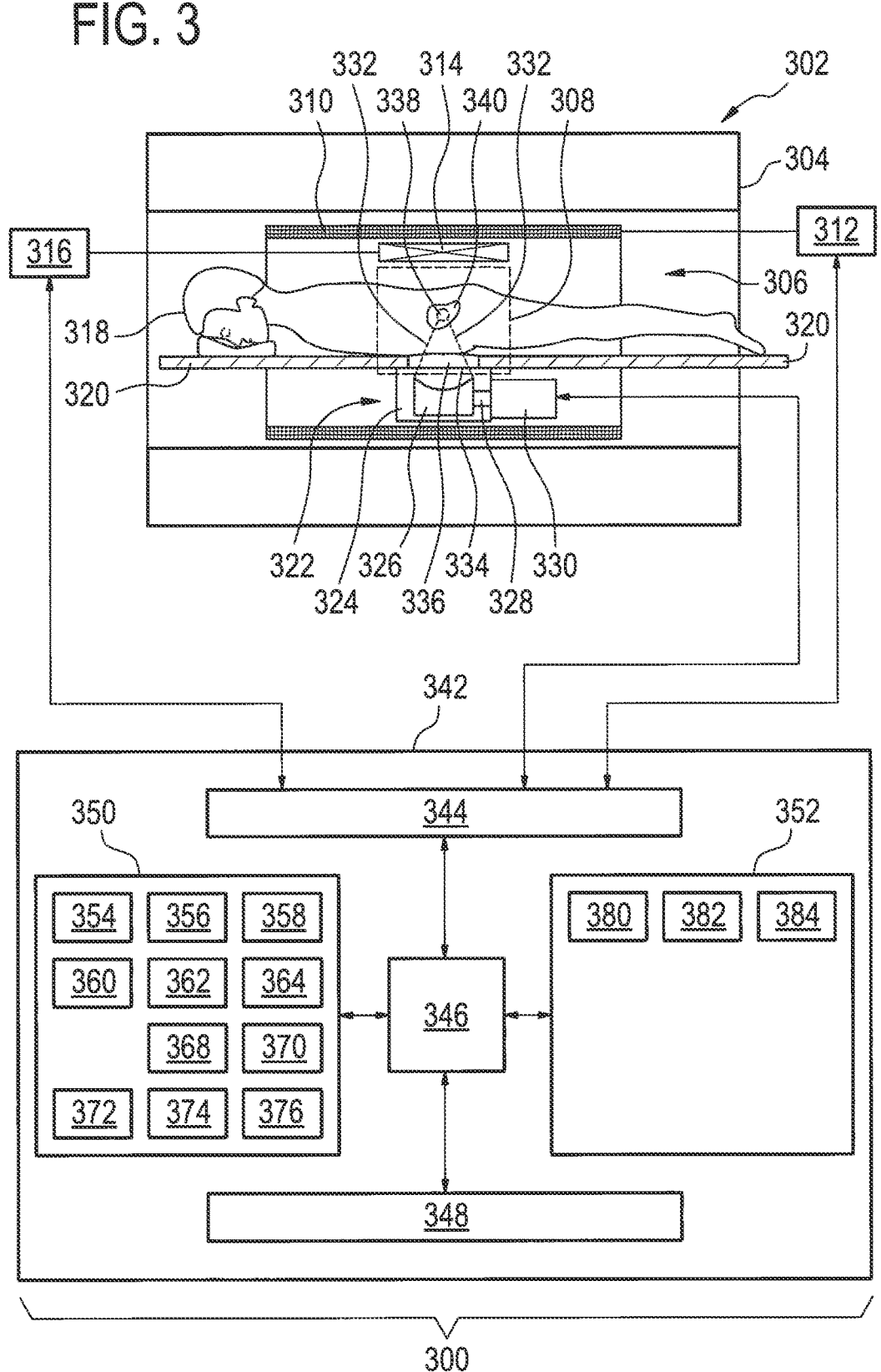
FIG. 3 shows an embodiment of a medical apparatus according to an embodiment of the invention.

FIG. 3 shows an embodiment of a medical apparatus 300 according to an embodiment of the invention. The medical apparatus 300 comprises a magnetic resonance imaging system 302. The magnetic resonance imaging system comprises a magnet 304. The magnet 304 is a cylindrical type superconducting magnet with a bore 306 through the center of it. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the cylindrical magnet there is an imaging zone 308 where the magnetic field is strong and uniform enough to perform magnetic resonance imaging.

Within the bore 306 of the magnet there is also a set of magnetic field gradient coils 310 which are used for acquisition of magnetic resonance data to spatially encode magnetic spins within the imaging zone 308 of the magnet 304. The magnetic field gradient coils are connected to a magnetic field gradient coil power supply 312. The magnetic field gradient coils 310 are intended to be representative. Typically magnetic field gradient coils contain three separate sets of coils for spatially encoding in three orthogonal spatial directions. A magnetic field gradient power supply 312 supplies current to the magnetic field gradient coils 310. The current supplied to the magnetic field coils is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone. The radio-frequency coil may contain multiple coil elements. The radio-frequency coil may also be referred to as a channel or an antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio-frequency transceiver 316 are representative. The radio-frequency coil 314 is intended to also represent a dedicated transmit antenna and a dedicated receive antenna. Likewise the transceiver 316 may also represent a separate transmitter and receivers.

A subject 318 is shown as reposing on a subject support 320 and is located partially within the imaging zone 308. The embodiment shown in FIG. 3 comprises a high-intensity focused ultrasound system 322. The high-intensity focused ultrasound system comprises a fluid-filled chamber 324. Within the fluid-filled chamber 324 is an ultrasound transducer 326. Although it is not shown in this figure the ultrasound transducer 326 may comprise multiple ultrasound transducer elements each capable of generating an individual beam of ultrasound. This may be used to steer the location of a sonication point 338 electronically by controlling the phase and/or amplitude of alternating electrical current supplied to each of the ultrasound transducer elements.

The ultrasound transducer 326 is connected to a mechanism 328 which allows the ultrasound transducer 326 to be repositioned mechanically. The mechanism 328 is connected to a mechanical actuator 330 which is adapted for actuating the mechanism 328. The mechanical actuator 330 also represents a power supply for supplying electrical power to the ultrasound transducer 326. In some embodiments the power supply may control the phase and/or amplitude of electrical power to individual ultrasound transducer elements. In some embodiments the mechanical actuator/power supply 330 is located outside of the bore 306 of the magnet 304.

The ultrasound transducer 326 generates ultrasound which is shown as following the path 332. The ultrasound 332 goes through the fluid-filled chamber 324 and through an ultrasound window 334. In this embodiment the ultrasound then passes through a gel pad 336. The gel pad 336 is not necessarily present in all embodiments but in this embodiment there is a recess in the subject support 320 for receiving a gel pad 336. The gel pad 336 helps couple ultrasonic power between the transducer 326 and the subject 318. After passing through the gel pad 336 the ultrasound 332 passes through the subject 318 and is focused to a sonication point 338. The sonication point 338 is being focused within a target volume 340. The sonication point 338 may be moved through a combination of mechanically positioning the ultrasonic transducer 326 and electronically steering the position of the sonication point 338 to treat the entire target volume 340.

The magnetic field gradient coil power supply 312, the transceiver 316, and the mechanical actuator/power supply 330 of the high-intensity focused ultrasound system 322 are shown as being connected to a hardware interface 344 of computer 342. The computer 342 further comprises a processor 346, a user interface 348, computer storage 350, and computer memory 352. The hardware interface 344 enables the processor 346 to send and receive commands and data in order to control the functioning of the medical apparatus 300. The processor 346 is further connected to the user interface 348, the computer storage 350, and the computer memory 352.

The computer storage 350 is shown as containing one or more pulse sequences 354. A pulse sequence as used herein encompasses a sequence of commands which enables the processor 346 to acquire magnetic resonance data 356 using the magnetic resonance imaging system 302. The computer storage 350 is further shown as containing magnetic resonance data 356. The magnetic resonance data 356 may be divided into subsampled magnetic resonance data 358 and image magnetic resonance data 360 in some embodiments. The computer storage 350 further shows a magnetic resonance image 362 reconstructed from the image magnetic resonance data 360. The computer storage 350 is further shown as containing a k-space sampling pattern 364. The k-space sampling pattern 364 may be used in some embodiments to select the k-space points or regions for acquiring the subsampled magnetic resonance data 358.

The computer storage 350 is further shown as containing magnetic resonance navigator data 368. The magnetic resonance navigator data 368 may be used in some embodiments as the magnetic resonance data used for controlling the high-intensity focused ultrasound system 322. The computer storage 350 further contains high-intensity focused ultrasound system control commands 370. These commands 370 enable the processor 346 to control the operation and function of the high-intensity focused ultrasound system 322. The computer storage 350 is further shown as containing a treatment plan 372. The treatment plan as used herein may contain anatomical data and/or plans entered by an operator or a physician for the detailed sonication of the target volume 340. The computer storage 350 is further shown as containing magnetic resonance thermometry data 374. The magnetic resonance thermometry data 374 may be the magnetic resonance data 356 acquired such that thermal or energy deposition maps 376 may be calculated. The computer storage 350 is further shown as containing an energy deposition map 376.

The computer memory 352 is shown as containing magnetic resonance imaging system control program 380. The program 380 contains computer executable code which enables the processor 346 to acquire the magnetic resonance data 356 using a pulse sequence 354. The computer memory 352 is shown as further containing a sonication control program 382. The sonication program 382 uses magnetic resonance data such as the magnetic resonance data 356, the subsampled magnetic resonance data 358, and/or the magnetic resonance navigator data 368 to generate high-intensity focused ultrasound system control commands 370. In some embodiments the sonication control program 382 may also use the magnetic resonance thermometry data 374 to make an intermediate energy deposition map 376 which is then used to generate the high-intensity focused ultrasound system control commands 370. The computer memory 352 is further shown as containing an image reconstruction software module 384. The image reconstruction software module may be used to generate a magnetic resonance image 362 from image magnetic resonance data 360.

In the embodiment shown in FIG. 3 the sonication control program 382 functions as the sonication control module for controlling the sonication of the target volume using the magnetic resonance data. The acquisition of magnetic resonance image data 360 and subsampled magnetic resonance data 358 may be routed to the sonication control program 382 and the image reconstruction software module 384 separately. This may enable a more rapid feedback loop between the acquisition of magnetic resonance data and the generation of high-intensity focused ultrasound system control commands 370.

Figure 4:
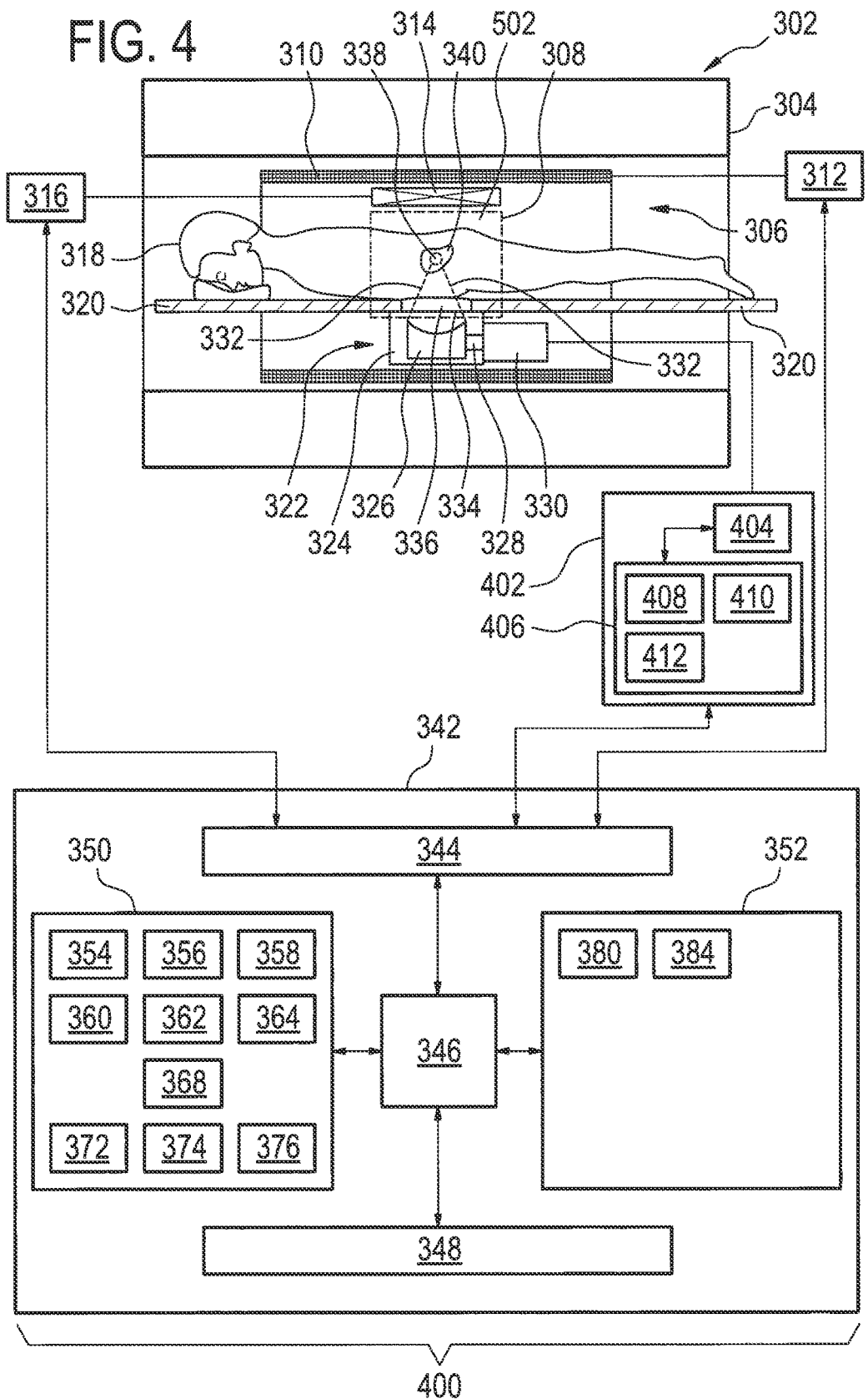
FIG. 4 shows a further embodiment of a medical apparatus according to an embodiment of the invention.

FIG. 4 shows an alternative embodiment of a medical apparatus 400 according to the invention. The embodiment shown in FIG. 4 is very similar to the embodiment shown in FIG. 3. However, in this embodiment a separate sonication control module 402 is used to control the high-intensity focused ultrasound system 322. The sonication control module 402 is shown as being networked to the hardware interface 344. The sonication control module 402 contains a processor 404 and a memory 406. Within the memory is a sonication control program 408. Sonication control program 408 is equivalent to sonication control program 382. The computer memory 406 is further shown as containing subsampled magnetic resonance data 410. The subsampled magnetic resonance data 410 is subsampled magnetic resonance data acquired by the magnetic resonance imaging system 302 which is streamed to the sonication control module 402 in real time. The computer memory 406 further shows high-intensity focused ultrasound system control commands 412. The high-intensity focused ultrasound system control commands 412 are equivalent to the high-intensity focused ultrasound system control commands 370.

The processor 404 may then send the high-intensity focused ultrasound system control commands 412 to the high-intensity focused ultrasound system 322 to control it in real time.

Figure 5:
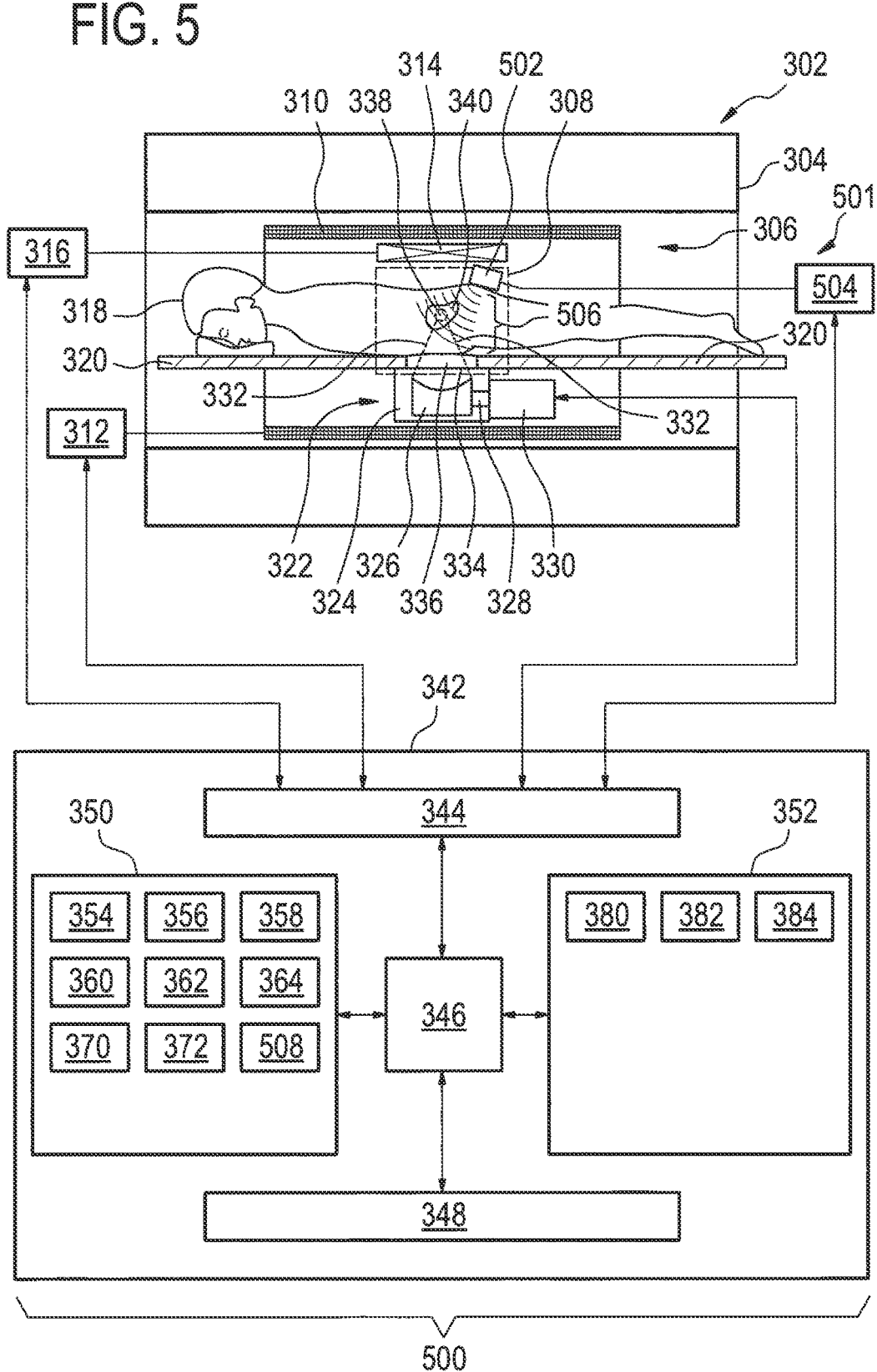
FIG. 5 shows a further embodiment of a medical apparatus according to an embodiment of the invention.

FIG. 5 shows a medical apparatus 500 according to a further embodiment of the invention. The embodiment shown in FIG. 5 is similar to the embodiment shown in FIG. 3. However this embodiment has the addition of a elastographic ultrasound system 501. The elastographic ultrasound system 501 comprises an ultrasonic transducer 502 and an ultrasonic power supply 504. The ultrasonic transducer 502 is shown in contact with the subject 318. Ultrasonic waves 506 propagate from the ultrasonic transducer 502 to the target volume 340. As tissue is sonicated in the sonication point 338 the tissue properties change. The ultrasonic waves 506 cause the tissue to vibrate by detecting the elastographic properties of the tissue using magnetic resonance imaging regions which have been sufficiently sonicated can be detected. The computer storage 350 is shown as containing a tissue elasticity map 508 which was constructed by the sonication control program 382. The tissue elasticity map 508 is then used by the sonication control program 382 for the generation of the high-intensity focused ultrasound system control commands 370. Some features of FIG. 4 such as the complete sonication control module 402 may also be incorporated into the embodiment shown in FIG. 5.

Fast thermal image feedback for steering focused ultrasound in moving and/or rapidly heating tissue is needed to produce sharply delineated necrosis and to prevent collateral tissue damage. However, the current state-of-art reconstructed images from diagnostic scanners do not have well-defined time-characteristics and are optimized for reconstructing diagnostically valuable image data, which can introduce further delays in image acquisition.

According to a further embodiment of the invention, the feedback loop—formed by data-acquisition, data analysis, feedback command creation, and feedback application—is carried in real-time domain in entirety, whereby the scanner image reconstruction is by-passed and replaced with a real-time reconstruction software running on a soft or hard real-time operating system and the reconstructed data is converted to format pertinent for feedback in the real-time domain.

According to a further embodiment of the invention, the format pertinent for feedback does not need to be diagnostically usable, and a secondary, possibly non-real time reconstruction or routing component may produce diagnostically viewable data at a more leisurely pace.

According to a further embodiment of the invention acquired data from the target volume(s) spans three-dimensional physical volume(s) where heating, movement, or tissue changes are pertinent for the feedback.

According to a further embodiment of the invention, acquired data contains interleaved sections for feedback and for diagnostically viewable data, and the diagnostically viewable data, possibly supported with the feedback data, is routed to a reconstruction algorithm that does not harm the real-time performance of the actual feedback loop.

The invention defines a method for reliable feedback for target volumes. The method is particularly useful for Magnetic Resonance (MR)-guided High Intensity Focused Ultrasound therapy, where the diagnostic MR scanner hardware produces real-time data directly into the HIFU system, by-passing the diagnostic MR data handling.

In a further embodiment, a Magnetic Resonance Imaging (MRI) scanner is integrated with a High Intensity Focused Ultrasound (HIFU) system so that the real-time MR data acquisition system is daisy-chained to dispatch raw data, such as the physiology signals from cardiac and respiratory sensors, gradient waveforms, and sampled k-space vectors, to the HIFU system. HIFU system is equipped with a soft real-time Linux server that can receive the daisy-chained data:

1) The data is converted into internal data structures and passed on to reconstruction algorithms.

2) Reconstruction algorithms produce output for routing the data for viewing and for deducing the feedback values.

3)
 a. A lower-priority algorithm reconstructs viewing images to be dispatched to a non-real-time user interface.
 b. A higher-priority algorithm deduces the trajectory and power updates for HIFU transmissions and dispatches the data to the hardware for application.

In a further embodiment of the invention, the daisy-chained diagnostic reconstruction accepts the incoming data, save the interleaved feedback data. As a result, the diagnostic images for viewing are acquired from the diagnostic scanner, similarly to what is currently done in the art, but the feedback data is concurrently routed through the real-time components, effectively separating the data paths.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 300 medical apparatus
302 magnetic resonance imaging system
304 magnet
306 bore of magnet
308 imaging zone
310 magnetic field gradient coils
312 magnetic field gradient coils power supply
314 radio-frequency coil
316 transceiver
318 subject
320 subject support
322 high intensity focused ultrasound system
324 fluid filled chamber
326 ultrasound transducer
328 mechanism
330 mechanical actuator/power supply
332 path of ultrasound
334 ultrasound window
336 gel pad
338 sonication point
340 target volume
342 computer system
344 hardware interface
346 processor
348 user interface
350 computer storage
352 computer memory
354 pulse sequence
356 magnetic resonance data
358 subsampled magnetic resonance data
360 image magnetic resonance data
362 magnetic resonance image
364 k-space sampling pattern
368 magnetic resonance navigator data
370 high intensity focused ultrasound system control commands
372 treatment plan
374 magnetic resonance thermometry data
376 energy deposition map
380 magnetic resonance imaging system control program
382 sonication control program
384 image reconstruction software module
400 medical apparatus
402 sonication control module
404 processor
406 computer memory
408 sonication control program
410 subsampled magnetic resonance data
412 high intensity focused ultrasound system control commands
500 medical apparatus
501 elastographic ultrasound system
502 ultrasonic transducer
504 ultrasonic power supply
506 ultrasonic waves
508 tissue elasticity map

The invention claimed is:

1. A medical apparatus comprising:
a high intensity focused ultrasound (HIFU) system configured to generate focused ultrasonic energy for sonicating a target volume of a subject;
a magnetic resonance imaging system configured to acquire magnetic resonance data from an imaging zone, wherein the target volume is within the imaging zone; and
a processor configured to control the medical apparatus using executable instructions stored in a non-transitory memory, wherein execution of the instructions causes the processor to repeatedly:
acquire the magnetic resonance data in real time using the magnetic resonance imaging system;
control the sonication of the target volume by controlling the HIFU system to generate focused ultrasonic energy for sonicating, in real time using the magnetic resonance data, the magnetic resonance data comprising subsampled magnetic resonance data and image magnetic resonance data, using at least the subsampled magnetic resonance data as a control parameter for controlling the sonication of the target volume, wherein the magnetic resonance imaging system acquires the subsampled magnetic resonance data and image magnetic resonance data in an interleaved fashion, and wherein the subsampled magnetic resonance data is subsampled in comparison to the image magnetic resonance data and acquired more rapidly than the image magnetic resonance data; and control the reconstruction of the magnetic resonance image using the image magnetic resonance data.

2. The medical apparatus of claim 1, wherein the subsampled magnetic resonance data is subsampled by under sampling of k-space.

3. The medical apparatus of claim 2, wherein the under sampling of the k-space is non-uniformly distributed in the k-space.

4. The medical apparatus of claim 2, wherein the under sampling of the k-space is performed using a predetermined sampling pattern or a random sampling pattern.

5. The medical apparatus of claim 2, wherein the under sampling of the k-space is performed by sampling k-space elements determined by a Poisson-disk distribution.

6. The medical apparatus of claim 2, wherein the under sampling of the k-space is performed by sampling the k-space within a predetermined region of the k-space.

7. The medical apparatus of claim 2, wherein the under sampling of the k-space is performed by sampling fully a kernel of the k-space below a predetermined value of k and sparsely sampling above the predetermined value of k.

8. The medical apparatus of claim 1, wherein the subsampled magnetic resonance data comprises magnetic resonance navigator data.

9. The medical apparatus of claim 1, further comprising an elastrographic ultrasound system, wherein execution of the instructions further causes the processor to activate the elastrographic ultrasound system when acquiring at least a portion of the magnetic resonance data, and wherein execution of the instructions further causes the processor to use at least the portion of the magnetic resonance data acquired when the elastrographic ultrasound system was active for controlling the sonication of the target volume.

10. The medical apparatus of claim 1, wherein execution of the instructions further causes the processor to repeatedly calculate an energy deposition map using the magnetic resonance data, wherein the sonication control module is further configured to determine sonication trajectories and timing values in accordance with the energy deposition map.

11. The medical apparatus of claim 1, wherein execution of the instructions further causes the processor to broadcast the magnetic resonance data to the sonication control module.

12. The medical apparatus of claim 1, wherein execution of the instructions further causes the processor to control the high intensity focused ultrasound system without generating images from the magnetic resonance data.

13. The medical apparatus of claim 1, wherein the subsampled magnetic resonance data comprises undersampled magnetic resonance data.

14. The medical apparatus of claim 1, wherein the subsampled magnetic resonance data comprises magnetic resonance data without a high-frequency component of k-space.

15. A method of operating a medical apparatus, the medical apparatus comprising a high intensity focused ultrasound (HIFU) system configured for generating focused ultrasonic energy for sonicating a target volume of a subject, and a magnetic resonance imaging system for acquiring magnetic resonance data from an imaging zone, the target volume being within the imaging zone, the method comprising:

acquiring magnetic resonance data in real time using the magnetic resonance imaging system, the acquired magnetic resonance data including subsampled magnetic resonance data and image magnetic resonance data, acquired in an interleaved fashion;

controlling, by a processor, the sonication of the target volume by controlling the HIFU system configured for generating focused ultrasonic energy for sonicating, in real time using at least the subsampled magnetic resonance data as a control parameter, wherein the subsampled magnetic resonance data is subsampled in comparison to the image magnetic resonance data and acquired more rapidly than the image magnetic resonance data; and repeatedly reconstructing by the processor a magnetic resonance image using the image magnetic resonance data.

16. A non-transitory computer program product comprising machine executable instructions for execution by a processor controlling a medical apparatus, the medical apparatus comprising a high intensity focused ultrasound (HIFU) system configured for generating focused ultrasonic energy for sonicating a target volume of a subject, and a magnetic resonance imaging system for acquiring magnetic resonance data from an imaging zone, the target volume being within the imaging zone, execution of the instructions causing the processor to repeatedly:

acquire magnetic resonance data in real time using the magnetic resonance imaging system, the magnetic resonance data including subsampled magnetic resonance data and image magnetic resonance data, acquired in an interleaved fashion;

control sonication of the target volume by controlling the HIFU system configured for generating focused ultrasonic energy for sonicating, in real time using the sonication control module and the subsampled magnetic resonance data as a control parameter, wherein the subsampled magnetic resonance data is subsampled in comparison to the image magnetic resonance data and acquired more rapidly than the image magnetic resonance data; and reconstruct a magnetic resonance image using an image reconstruction module and the image magnetic resonance data.

* * * * *